United States Patent [19]
Gilbard et al.

[11] Patent Number: 4,868,154
[45] Date of Patent: Sep. 19, 1989

[54] STIMULATION OF TEAR SECRETION WITH MELANOCYTE STIMULATING HORMONES

[75] Inventors: Jeffrey P. Gilbard, Boston; Darlene A. Dartt, Newton, both of Mass.

[73] Assignee: Eye Research Institute of Retina Foundation, Boston, Mass.

[21] Appl. No.: 830,675

[22] Filed: Feb. 19, 1986

[51] Int. Cl.$^4$ .............................................. A61K 37/24
[52] U.S. Cl. ......................................... 514/13; 514/14; 514/912; 514/915; 424/427; 424/429; 424/450
[58] Field of Search .................. 514/13, 14, 912, 915; 424/429, 427, 450

[56] References Cited

U.S. PATENT DOCUMENTS 3,991,759  11/1976  Urquhart ............................. 424/427

FOREIGN PATENT DOCUMENTS 3668084  6/1985  Australia .

OTHER PUBLICATIONS

The Handbook of Non-Prescription Drugs, Fifth Ed., 1977, pp. 232, 241 and 244.
Dyster et al., "Melanocyte Stimulating Activity in Serum and the Aqueous Flair Response in Rabbits", 46(2), J. Endocrinol., pp. 285-286, (1970).
Green and Elijah, "Drug Effects on Aqueous Humor Formation and Pseudo Facility in Normal Rabbit Eyes", 33 Exp. Eye Res., pp. 239-245, (1981).
Dartt et al., Lacrimal Gland Electrolyte and Water Secretion in the Rabbit: Localization and Role of (Na$^+$+K$^+$) Activated ATPase, J. Physiol., (1981), 321:559-569.
Dartt, Cellular Control of Protein Electrolyte, and Water Secretion by the Lacrimal Gland, in *The Preoccular Tear Film in Health, Disease and Contact Lens Wear*, (F. J. Holly, Ed.), Dry Eye Institute, Inc., Lubbock, Tex., (1986), pp. 358-370.
Friedman et al., β-Adrenergic Receptor Stimulated Peroxide Secretion from Rat Lacrimal Gland, Biochem. Biophys. Acta, (1981), 675:40-45.
Gilbard and Dartt, Changes in Rabbit Lacrimal Gland Fluid Osmolarity with Flow Rate, Invest. Ophthalmoh. Vis. Sci., (1982), 23:804-806.
Mauduit et al., Protein Secretion Induced by Isoproterenol or Pentoxifylline in Lacrimal Gland: Ca$^{2+}$ Effects, Am. J. Physiol., (1984), 246:C37-C44.
Stolze and Sommer, Effect of Different Scretagogues in Rabbit Lacrimal Gland Protein Scretion, in *The Preoccular Tear Film in Health, Disease and Contact Lens Wear*, (F. J. Holly, ed.), Dry Eye Institute, Inc., Lubbock, Tex., (1986), pp. 409-416.
"Alpha-Adrenergic Pathway for Stimulation of Lacrimal Gland Protein Secretion", (Cornea Conference, 11/1 and 11/2/85), Dartt et al.
"Vasoactive Intestinal Polypeptide Stimulation of Protein Secretion from Rat Lacrimal Gland Acini" Am. J. Physiol. 247:G502-G509 (1984), Dartt et al.
"Receptor for Secretagogues on Pancreatic Acinar Cells" J. of Physiol 238:G63-G66, (1980) Gardner and Jensen.
"Adrenocortiocotropic Hormone and Alpha-Melanocyte-Stimulating Hormone Induce Secretion and Protein Phosphorylation in the Rat Lacrimal Gland by Activation of a cAMP-Dependent Pathway", Eur. J. Biochem, 126:623-629, (1982) John et al.
"Ultrastructural Localization of VIP-Like Immunoreactivity in Large Dense-Core Vesicles of Choliner- (List continued on next page.)

*Primary Examiner*—Johnnie R. Brown
*Assistant Examiner*—Jacqueline M. Stone
*Attorney, Agent, or Firm*—Lahive & Cockfield

[57] ABSTRACT

A method and preparation for the stimulation of tear secretion. The method involves topically applying to the ocular surface melanocyte stimulating hormones, and their active precursors, derivatives, and fragments which activate melanotropin receptors of lacrimal gland tissue. The preparation contains a melanocyte stimulating hormone, and a vehicle for a melanocyte stimulating hormone and may also contain an ophthalmic preservative.

7 Claims, 2 Drawing Sheets

OTHER PUBLICATIONS gic-Type Nerve Terminals in Cat Exocrine Glands" Neuroscience 6:847-862 (1981), Johansson and Lundberg.

"Vasoactive Intestinal Peptide Stimulates Outward Current in Single Lacrimal Acini Cells from Rat" Supplement to Investigative Ophthalmology & Visual Science 27(3) Mar. 1986, Lechleiter et al.

"Effect of Different Secretogogues on Lacrimal Protein Pattern", (International Tear Film Sumposium, 1984, Lubbock, Tex.), Stolze and Sommer.

"Influence of Secretagogues on Volume and Protein Pattern in Rabbit Lacrimal Fluid": Current Eye Research, vol. 4, No. 4, pp. 489-492 (1985) Stolze and Somer.

"Stimulation of Retinol Secretion in Lacrimal Gland Fluid by Acetylcoline and Vasoactive Intestinal Peptice (VIP)" (Cornea Conference 11/1 & 11/2/85), Ubels et al.

"Correlation of Secretion of Retinol and Protein by the Lacrimal Gland" Supplement to Investigative Ophthalmology & Visual Science 27(3), Mar. 1986, Ubels et al.

"Vasoactive Intestinal Peptide Nerves in Ocular and Orbital Structures of the Cat" Invest. Ophthlamol. Vis. Sci., 19:878-885 (1980), Uddman et al.

Green et al., cited in Biol. Abstracts 73(5):3566, Ref. No. 34593, 1981.

STIMULATION OF TEAR SECRETION WITH MELANOCYTE STIMULATING HORMONES

BACKGROUND OF THE INVENTION

This invention was made with Government support under EY 03373 awarded by The National Eye Institute, and the Federal Government has limited rights therein.

This invention relates to a method and preparation for stimulating tear secretion. More particularly, it relates to the stimulation of tear secretion with topically applied melanocyte stimulating hormones which activate the melanotropin receptors of lacrimal gland tissue There are a number of situations where it is desirable to increase the amount and/or to modify the nature of tear fluid produced by the eye. Illustrative instances include the treatment of a spectrum of dry eye disorders including, but not limited to, keratoconjunctivitis sicca, age-related dry eye, Stevens-Johnson syndrome, ocular cicatricial pemphigoid, blepharitis, neurotrophic ocular surface disease and corneal exposure. In addition, patients who wear contact lenses may have sub-optimal rates of tear production for optimal contact lens wear. Increased tear production is likely to increase eye comfort and, contact lens comfort, and improve contact lens wear. These patients will therefore benefit from agents that could increase tear production.

The lacrimal gland is an exocrine gland that secretes protein, as well as, by different mechanisms, water and electrolytes. To stimulate secretion, agonists increase the intracellular free calcium concentration and/or the cyclic AMP level. However, protein is secreted by exocytosis, whereas electrolytes and water are secreted as the permeability of cell membranes is selectively increased to sodium, potassium and chloride. A given agonist could stimulate water and electrolyte secretion, but not protein secretion, and visa versa.

The topical administration of a vasoactive intestinal peptide stimulates lacrimal gland fluid secretion (Gilbard and Dartt, patent pending) and is known to increase cyclic AMP levels in lacrimal gland cells (Dartt et al, Am. J. Physio. 247: G502, 1984). The administration of adrenocorticotropic hormone as well as alpha melanocyte stimulating hormone (alpha-MSH) to tissue pieces in vitro has been shown to stimulate protein secretion. The data suggests that the actions of adrenocorticotropic hormone and of alpha-MSH are mediated by cAMP as a "second messenger." (Jahn et al Eur. J. Biochem 126: 623, 1982).

A topical mode of administration has several advantages. It eliminates the need for injections in patients with dry eye disorders, and thereby decreases untoward systemic effects, cost of therapy, and the amount of drug needed.

Accordingly, it is an object of this invention to provide an improved method for stimulating tear secretion by topical administration. It is another object of this invention to provide an improved method of stimulating lacrimal gland secretion by topical application of compounds to the ocular surface. It is also an object to provide an improved method for the treatment of dry eye disorders. Another object of the present invention is to facilitate the treatment of dry eye disorders by eliminating the need for systemic therapy such as injection. A further object is to provide an improved agent for topical application to improve eye comfort. It is another object of the present invention to provide an improved agent for topical application to enhance contact lens wear and comfort. A further object is to provide a method for increasing the amount of the tear fluid produced by lacrimal glad tissue. Other objects of the invention will in part be obvious and will in part appear hereinafter.

SUMMARY OF THE INVENTION

In accordance with the invention, it has been found that melanocyte stimulating hormones effectively stimulate tear secretion when applied topically to the eye. The method for stimulating tear secretion is useful for the treatment of dry eye disorders, and it facilitates such treatment by eliminating the need for injections. Also a corresponding preparation has been found which when applied topically stimulates lacrimal glad secretion. The preparation contains a melanocyte stimulating hormone and an ophthalmic preservative and typically contains a physiologically compatible vehicle.

The method involves topical administration to the ocular surface of compounds that activate melanotropin receptors of lacrimal glad tissue to stimulate tear secretion. These compounds include alpha-melanocyte stimulating hormone (alpha-MSH), beta-melanocyte stimulating hormone (beta-MSH), and gamma-melanocyte stimulating hormone (gamma MSH) and their active precursors, derivatives, and fragments. These compounds may be used alone or in combination with one another.

Several mode of topical administration may be used in the practice of the invention. For example, the compounds may be administered topically to the eye as a drop, or within ointments, gels, or liposomes Further, compounds may be infused into the tear film by means of a pump-catheter system. In other embodiments the compounds are attached to and/or incorporated into or carried by contact lenses or contained within continuous or other selective-release devices including membranes, and thereby contact the ocular surface.

The development of the foregoing agents that are effective in stimulating lacrimal secretion when applied topically to the eye is unexpected for several reasons. First, the main lacrimal gland is not exposed to the surface of the eye and lies separated from the ocular surface by a relatively great diffusion distance The main lacrimal gland is connected to the surface only through a series of microscopic ducts. Therefore, while drugs injected vascularly can reach the main lacrimal gland parenchyma, it is considered unlikely that topically applied drugs will do so. Second, although there are microscopic nests of accessory lacrimal gland tissue within the conjunctiva, one expects that drugs will not penetrate the luminal tight junctions of the duct and acinar cells to the deep basolateral membranes. It is assumed, based on study of the pancreas, that the receptors that initiate secretion are located in the deep basolateral membranes. Third, given that the accessory glands are thought to function somewhat independently from the main lacrimal gland, it is deemed unlikely that drugs that stimulate the main gland would stimulate the accessory glands even if penetration were adequate. Finally, one would expect that insufficient lacrimal tissue mass will preclude the success of an approach that seeks to act merely on the accessory glands.

BRIEF DESCRIPTION OF THE DRAWINGS

FIGS. 1S, 1B, and 1C represent results obtained from practice of the invention with rabbits

FIG. 1B is a graph of the osmolality of tear samples as a function of time taken from a rabbit eye treated with buffer solution and, subsequently, the same eye treated in accordance with the invention with buffer solution containing $10^{-5}M$ alpha-MSH.

FIG. 1C is a graph of the osmolality of tear samples as a function of time taken from a rabbit eye treated with buffer solution and, subsequently, the same eye treated in accordance with the invention with buffer solution containing $10^{-4}M$ alpha-MSH.

FIG. 2A is a graph of the osmolality of tear samples as a function of time taken from a rabbit eye treated with buffer solution and, subsequently, the same eye treated in accordance with the invention with buffer solution containing $10^{-5}M$ beta-MSH.

FIG. 2B is a graph of the osmolality of tear samples as a function of time taken from a rabbit eye treated with buffer solution and, subsequently, the same eye treated in accordance with the invention with buffer solution containing $10^{-4}M$ beta-MSH.

FIG. 2C is a graph of the osmolality of tear samples as a function of time taken from a rabbit eye treated with buffer solution and, subsequently, the same eye treated in accordance with the invention with buffer solution containing $10^{-3}M$ beta-MSH.

FIG. 3A is a graph of the osmolality of tear samples as a function of time taken from a rabbit eye treated with buffer solution and, subsequently, the same eye treated in accordance with the invention with buffer solution containing $10^{-5}M$ beta-MSH.

FIG. 3B is a graph of the osmolality of tear samples as a function of time taken from a rabbit eye treated with buffer solution and, subsequently, the same eye treated in accordance with the invention with buffer solution containing $10^{-4}M$ beta-MSH.

FIG. 3C is a graph of the osmolality of tear samples as a function of time taken from a rabbit eye treated with buffer solution and, subsequently, the same eye treated in accordance with the invention with buffer solution containing $10^{-3}M$ beta-MSH.

FIG. 4A is a graph of the osmolality of tear samples as a function of time taken from a rabbit eye treated with buffer solution and, subsequently, the same eye treated in accordance with the invention with buffer solution containing $10^{-5}M$ gamma-MSH.

FIG. 4B is a graph of the osmolality of tear samples as a function of time taken from a rabbit eye treated with buffer solution and, subsequently, the same eye treated in accordance with the invention with buffer solution containing $10^{-4}M$ gamma-MSH.

FIG. 4C is a graph of the osmolality of tear samples as a function of time taken from a rabbit eye treated with buffer solution and subsequently, the same eye treated in accordance with the invention with buffer solution containing $10^{-3}M$ gamma-MSH.

DESCRIPTION OF THE INVENTION

Figure 1A:
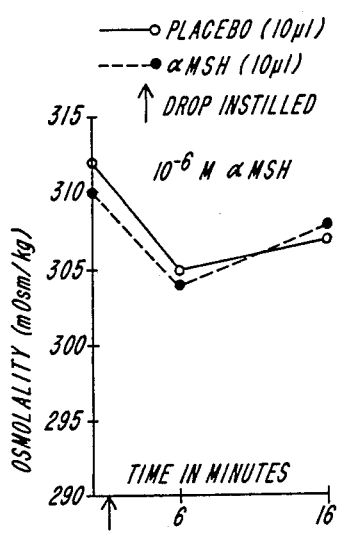
FIG. 1A is a graph of the osmolality of tear samples as a function of time taken from a rabbit eye treated with buffer solution and, subsequently, the same eye treated in accordance with the invention with buffer solution containing $10^{-6}M$ (molar) alpha-MSH.

In accordance with the invention, tear secretion is stimulated with melanocyte stimulating hormones. More particularly, it has been found that melanocyte stimulating hormones and/or their active precursors, analogues, or derivatives applied topically to the ocular surface activate the melanotropin receptors of lacrimal gland tissue to stimulate tear secretion.

A preparation according to the invention can, by way of non-limiting illustration, be applied to the eye in animals and humans as a drop or within ointments, gels, or liposomes. Further, the compounds may be infused into the tear film via a pump-catheter system. In other embodiments the compounds can be contained within continuous or other selective-release devices, for example, membranes, such as but not limited to those used in the Ocusert ® system (Alza Corp., Palo Alto, Calif.). As a further specific example, the compounds can be attached to, carried by and/or contained within contact lenses that are placed on the eye. In general, it is desired that the compound enter the tear film or otherwise make contact with the surface of the eye In vivo examples in accordance with the invention were conducted on rabbits with dry eyes. The dry eye disorder is created by surgically closing the duct that carries fluid from the main lacrimal gland to the tear film and surgically removing the nictitans and harderian glands. This leaves intact only the accessory glands that lie on the surface of the eye. These rabbits develop increased tear film osmolality soon after the operation, a finding that is understood to be due to decreased tear production, and that is characteristic of dry eye. It is recognized that results of opthalmologic tests using rabbits has close correlation with humans and therefore the results carry over to humans The effect on tear film osmolality of topically applied isotonic buffer solution with and without melanocyte stimulating hormones which activate the melanotropin receptors was studied in the dry eye rabbit. All test drops were ten microliters ($\mu$l) in volume. Tear samples were taken with a micropipette system, in the manner described in the article entitled "Osmolarity of Tear Microvolumes in Keratoconjunctivitis Sicca", by Gilbard et al, Arch Ophthalmol 96:677, 1978. Osmolarity was measured by freezing-point depression.

The following protocol was used to test the effects of the topically applied melanotropins. At zero time a tear sample was taken for measurement of osmolality. At one minute the test drop was instilled. At six and at sixteen minutes, tear samples were taken for osmolality measurements. Five minutes after the sixteen minute sample, the above sequence was repeated several times to test additional drops.

The following drops were instilled in the test eye and after each such instillation, test samples were taken as stated: (1) buffer solution, (2) buffer solution containing a melanocyte stimulating hormone at a low dose, (3) buffer solution, (4) buffer solution containing a melanocyte stimulating hormone at a moderate dose, (5) buffer solution, (6) buffer solution containing a melanocyte stimulating hormone at a higher dose. The melanocyte stimulating hormone may be obtained from Peninsula Laboratories, Inc., Belmont California. The results are shown in FIGS. 1 through 4 A, B, and C, where FIGS.

1 through 4 each represent results obtained from the same rabbit.

Figure 1B:
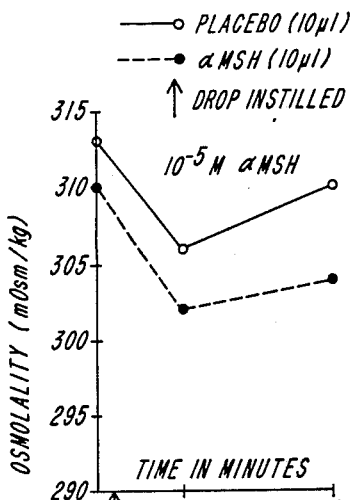
Figure 1C:
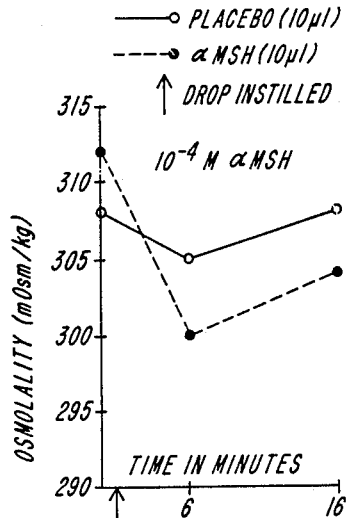

FIG. 1 represents results obtained using alpha-MSH. The concentrations of alpha-MSH given in the 10 $\mu$l drops were:

A) $10^{-6}$ M, B) $10^{-5}$ M, and C) $10^{-4}$ M. As shown in FIG. 1, buffer solution containing alpha-MSH lowers the tear film osmolality more effectively than buffer alone. The figure also indicates a dose-dependent decrease in tear film osmolality, and the decrease was strikingly more pronounced than the effect of the buffer alone. This reflects an alpha-MSH stimulated dose-dependent increase in tear secretion.

Figure 2A:
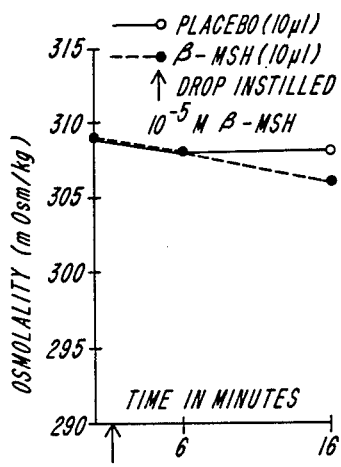
FIGS. 2A, 2B, and 2C represent results obtained from further practice of the invention with rabbits.
Figure 2B:
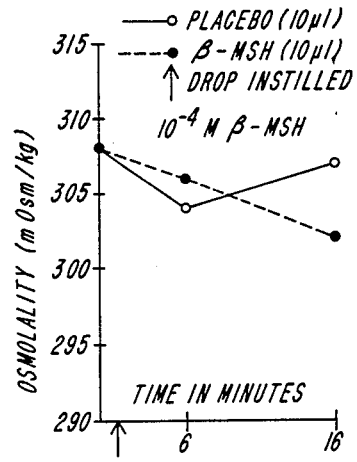
Figure 2C:
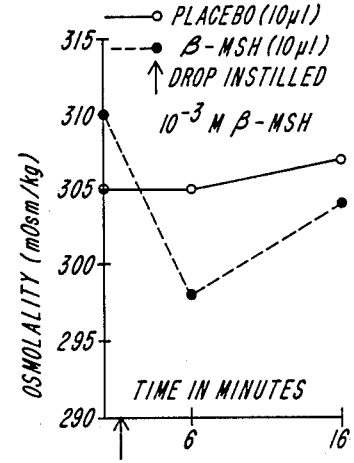
Figure 3A:
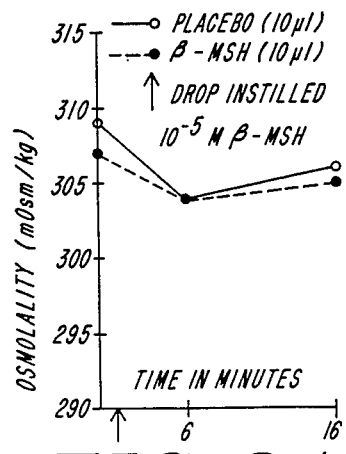
FIGS. 3A, 3B, and 3C represent results obtained from further practice of the invention with rabbits.
Figure 3B:
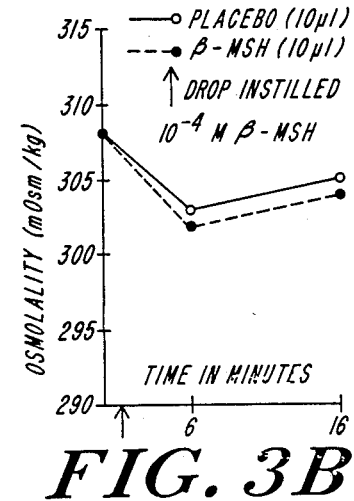
Figure 3C:
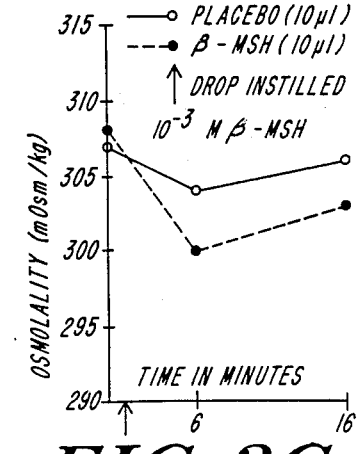

FIGS. 2 and 3 represent results obtained using beta-MSH. The concentration of beta-MSH given in the 10 $\mu$l drops were: A) $10^{-5}$ M, B) $10^{-4}$ M, and C) $10^{-3}$ M. As shown in FIGS. 2 and 3, buffer solution containing beta-MSH lowers the tear film osmolality more effectively than buffer alone. The Figures also indicate a dose-dependent decrease in tear film osmolality, and the decrease was strikingly more pronounced than the effect of the buffer alone. This reflects a beta-MSH stimulated dose-dependent increase in tear secretion.

Figure 4A:
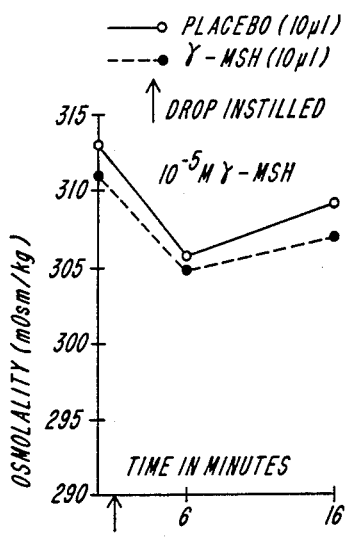
FIG. 4A, 4B and 4C represent results obtained from further practice of the invention with rabbits.
Figure 4B:
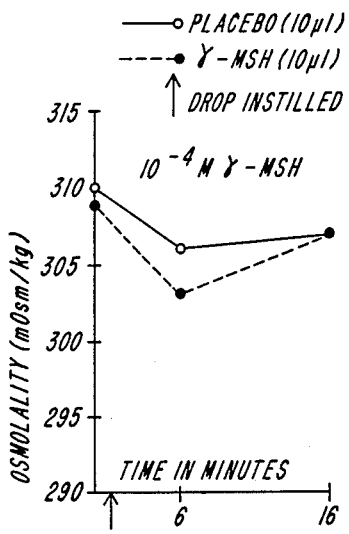
Figure 4C:
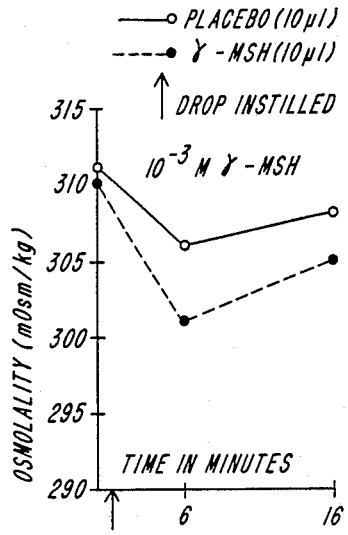

FIG. 4 represents results obtained using gamma-MSH The concentrations of gamma-MSH given in the 10 $\mu$l drops were: A) $10^{-5}$ M, B) $10^{-4}$ M, and C) $10^{-3}$ M. As shown in FIG. 4, buffer solution containing gamma-MSH lowers the tear film osmolality more effectively than buffer alone. The Figure also indicates a dose-dependent decrease in tear film osmolality, and the decrease was strikingly more pronounced than the effect of the buffer alone This reflects a gamma-MSH stimulated dose-dependent increase in tear secretion In further accordance with the invention, a topical tear secretion preparation is made by combining a melanotropin with an appropriate preservative. The preparation may also contain a physiologically compatible vehicle, as those skilled in the art can select using conventional criteria The vehicles may be selected from the known ophthalmic vehicles which include, but are not limited to water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride One preferred vehicle is the non-toxic ophthalmic preparation which has the following composition: about 22.0 to 43.0 millimoles of potassium per liter; about 29.0 to 50.0 millimoles of bicarbonate per liter; about 130.0 to 140.0 millimoles of sodium per liter; and about 118.0 to 136.5 millimoles o chloride per liter. Stated generally, both the vehicle and the preservative are to be physiologically compatible with the melanotropin and are not to inactivate the secretion-stimulating activity of the hormone.

In accordance with the invention one preservative free example of the preparation for installation in the eye in drop form contains melanocyte stimulating hormone, and the foregoing non-toxic ophthalmic preparation as a vehicle.

It will thus be see that the objects set forth above among those made apparent from the preceding description, are efficiently attained. Since certain changes may be made in carrying out the above method and in formulating the foregoing preparation without departing from the scope of the invention, it is intended that all matter contained in the above description shall be interpreted as illustrative and not in a limiting sense.

Accordingly, the invention may be embodied in other specific forms without departing from the scope or spirit thereof.

What is claimed is:

1. A sterile preparation adapted for topical administration to the eye comprising:
   an effective amount of a compound which activates the melanotropin receptors in said accessory lacrimal gland selected from a group consisting of alpha-melanocyte stimulating hormone, beta-melanocyte stimulating hormone, gamma-melanocyte stimulating hormone, and their active precursors, analogs, and derivatives; and
   a physiologically compatible vehicle selected from a group consisting of aqueous electrolyte solutions, polyethers, polyvinyls, polymers of acrylic acid, lanolin, glucosaminoglycans;
   whereby said preparation promotes fluid secretion from said accessory lacrimal glad without affecting the main lacrimal gland.

2. The preparation of claim 1 wherein said sterility is achieved by aseptic packaging.

3. The preparation of claim 1 further comprising an ophthalmic preservative to achieve said sterility.

4. A method of stimulating in vivo fluid secretion from human accessory lacrimal glands comprising the step of topical administration to the ocular surface of an effective amount of a preparation which includes a compound that activates the melanotropin receptors in said accessory lacrimal glands selected from a group consisting of alpha-melanocyte stimulating hormone, beta-melanocyte stimulating hormone, gamma-melanocyte stimulating hormone, and their active precursors, analogs, and derivatives.

5. The method of claim 4 wherein said topical administration comprises infusion of said preparation to said ocular surface from a device selected from a group consisting of a pump-catheter system, a selective release device, and a contact lens.

6. The method of claim 4 wherein said preparation for topical administration comprises a dispersion of said compound in a carrier vehicle selected from a group consisting of drops of liquid, gels, ointments, and liposomes.

7. The preparation of claim 3 wherein said compound comprises melanocyte stimulating hormone and said aqueous vehicle comprises: (a) between about 22.0 to 43.0 millimoles of potassium per liter; (b) between about 29.0 to 50.0 millimoles of bicarbonate per liter; (c) between about 130.0 to 140.0 millimoles of sodium per liter; and (d) be ween about 118.0 to 136.5 millimoles of chloride per liter.

* * * * *